(12) United States Patent
Wine et al.

(10) Patent No.: US 12,053,613 B2
(45) Date of Patent: Aug. 6, 2024

(54) CIRCULAR ROLLER CLAMP ASSEMBLY

(71) Applicant: CareFusion 303, Inc., San Diego, CA (US)

(72) Inventors: Jason Andrew Wine, Placentia, CA (US); Tomas Frausto, Walnut, CA (US)

(73) Assignee: CAREFUSION 303, INC., San Diego, CA (US)

( * ) Notice: Subject to any disclaimer, the term of this patent is extended or adjusted under 35 U.S.C. 154(b) by 162 days.

(21) Appl. No.: 17/969,080

(22) Filed: Oct. 19, 2022

(65) Prior Publication Data

US 2023/0149628 A1 May 18, 2023

Related U.S. Application Data

(60) Provisional application No. 63/279,959, filed on Nov. 16, 2021.

(51) Int. Cl.
*A61M 5/168* (2006.01)
*A61M 39/28* (2006.01)
*F16L 3/10* (2006.01)

(52) U.S. Cl.
CPC .... *A61M 5/16881* (2013.01); *A61M 5/16886* (2013.01); *A61M 39/28* (2013.01); *F16L 3/1041* (2013.01); *A61M 2205/103* (2013.01)

(58) Field of Classification Search
CPC .......... A61M 5/16881; A61M 5/16886; A61M 39/28; A61M 2205/103; A61M 2205/10; A61M 2205/3334; A61M 2205/3561; A61M 2205/3576; A61M 2205/50; A61M 2205/8206; A61M 5/172; A61M 39/286; A61M 5/16813; A61M 5/16831; A61M 39/287; A61M 2205/3379; F16L 3/1041

USPC .......................................... 248/74.1
See application file for complete search history.

(56) References Cited

U.S. PATENT DOCUMENTS

| | | | |
|---|---|---|---|
| 7,074,212 B1* | 7/2006 | Florea | A61M 5/16881 604/246 |
| 2005/0027237 A1* | 2/2005 | Weiner | A61M 39/28 604/66 |
| 2016/0256628 A1* | 9/2016 | Lee | G05D 7/0617 |
| 2021/0031025 A1* | 2/2021 | McGee | A61M 5/16813 |
| 2021/0077806 A1* | 3/2021 | Park | A61M 39/286 |
| 2023/0149628 A1* | 5/2023 | Wine | A61M 39/28 248/74.1 |

(Continued)

OTHER PUBLICATIONS

International Search Report and Written Opinion for Application No. PCT/US2022/048460, dated Feb. 15, 2023, 57 pages.

*Primary Examiner* — Muhammad Ijaz
(74) *Attorney, Agent, or Firm* — Morgan, Lewis & Bockius LLP (57) ABSTRACT

A circular roller clamp assembly includes a semi-circular housing configured to receive a portion of an IV tube, a motor and a motor arm coupled to the motor. A roller is coupled to the roller arm, the roller movably received by a guide groove disposed in the semi-circular housing. A flow rate of fluid flowing through the IV tube is regulated based on roller impingement of the IV tube against a tube channel in the guide groove via circumferential movement of the roller along the guide groove. IV sets with circular roller clamp assemblies and methods of operating circular roller clamp assemblies are also provided.

20 Claims, 6 Drawing Sheets

(56) References Cited

U.S. PATENT DOCUMENTS

2024/0075207 A1\* 3/2024 Sanikommu ...... A61M 5/16813
2024/0123137 A1\* 4/2024 Ryan ................ A61M 5/16827

\* cited by examiner

- 210 — Pull roller away from roller clamp assembly
- 220 — Insert tubing into roller clamp assembly
- 230 — Release roller to engage tubing within tube channel
- 240 — Provide control signals to motor
- 250 — Move motor arm and roller to change tubing impingement for fluid flow adjustment

FIG. 10

CIRCULAR ROLLER CLAMP ASSEMBLY

CROSS-REFERENCE TO RELATED APPLICATIONS

This application claims the benefit of priority under 35 U.S.C. § 119 to U.S. Provisional Patent Application Ser. No. 63/279,959, entitled "CIRCULAR ROLLER CLAMP ASSEMBLY," filed on Nov. 16, 2021, the entirety of which is incorporated herein by reference.

TECHNICAL FIELD

The present disclosure generally relates to a gravity intravenous (IV) set or infusion pump flow control device, and in particular a circular roller clamp assembly.

BACKGROUND

Flow controllers in the form of roller clamps are used in the medical field for IV applications. Typical roller clamps control a flow rate through an IV tube by clamping the tube in between a roller wheel and a linear housing having a relatively short length. This approach, for one, provides a limited range of flow rate control because the roller wheel is essentially too sensitive in that a small movement of the roller wheel or dimension change causes a large change in flow rate of the fluid through the tube. Thus, the relatively course flow rate change provided by a typical roller clamp makes it difficult to provide precise flow control.

Also, typical roller clamps have flow rate drifting issues based on slippage of the roller wheel, such as when fluid pressure in the tube causes the roller wheel to roll back from the adjusted position. Further, typical roller clamps are manual devices that require a user, such as a health care clinician, to adjust the roller clamp by hand. In addition, typical roller clamps are not reusable devices and are disposed of with the rest of the IV set when the IV set is thrown out.

Thus, it is desirable to provide an automated roller wheel assembly that provides a large range of flow control resolution, allows for simple motor connections and eliminates or minimizes roller wheel slippage.

SUMMARY

In one or more embodiments, a circular roller clamp assembly comprises: a semi-circular housing configured to receive a portion of an IV tube; a motor; a motor arm coupled to the motor; and a roller coupled to the roller arm, the roller configured to be movably received by a guide groove disposed in the semi-circular housing, wherein the circular roller clamp assembly is configured to regulate a flow rate of fluid flowing through the IV tube based on engagement of the roller with the IV tube via circumferential movement of the roller along the guide groove.

In one or more embodiments, an IV set comprises: an IV tube configured to be coupled to a fluid container; an infusion component coupled to the IV tube; and a circular roller clamp assembly coupled to the IV tube, the circular roller clamp assembly comprising: a semi-circular housing configured to receive the IV tube; a motor; a motor arm coupled to the motor; and a roller coupled to the roller arm, the roller configured to be movably received by a guide groove disposed in the semi-circular housing, wherein the circular roller clamp assembly is configured to regulate a flow rate of fluid flowing through the IV tube based on engagement of the roller with the IV tube via circumferential movement of the roller along the guide groove.

In one or more embodiments, a method of operating a circular roller clamp assembly comprises: pulling a roller coupled to an extendable motor arm radially outward from a guide groove disposed in a perimeter surface of a semi-circular housing of the circular roller clamp assembly; placing an IV tube between roller and the guide groove; releasing the roller wherein a biasing force of a spring of the motor arm contracts the motor arm radially inward towards the IV tube and the guide groove; pressing, by the roller, the IV tube against a varying sized tube channel disposed within the guide groove; rotating, by a motor, the motor arm in a first direction to move the roller towards a smaller sized portion of the tube channel to increase impingement of the IV tube by the roller and decrease a rate of fluid flow through the IV tube; and rotating, by the motor, the motor arm in a second direction to move the roller towards a larger sized portion of the tube channel to decrease impingement of the IV tube by the roller and increase the rate of fluid flow through the IV tube.

The foregoing and other features, aspects and advantages of the disclosed embodiments will become more apparent from the following detailed description and accompanying drawings.

BRIEF DESCRIPTION OF THE DRAWINGS

The accompanying drawings, which are included to provide further understanding of the disclosure and are incorporated in and constitute a part of this specification, illustrate embodiments of the disclosure and together with the description serve to explain the principles of the disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Figure 1:
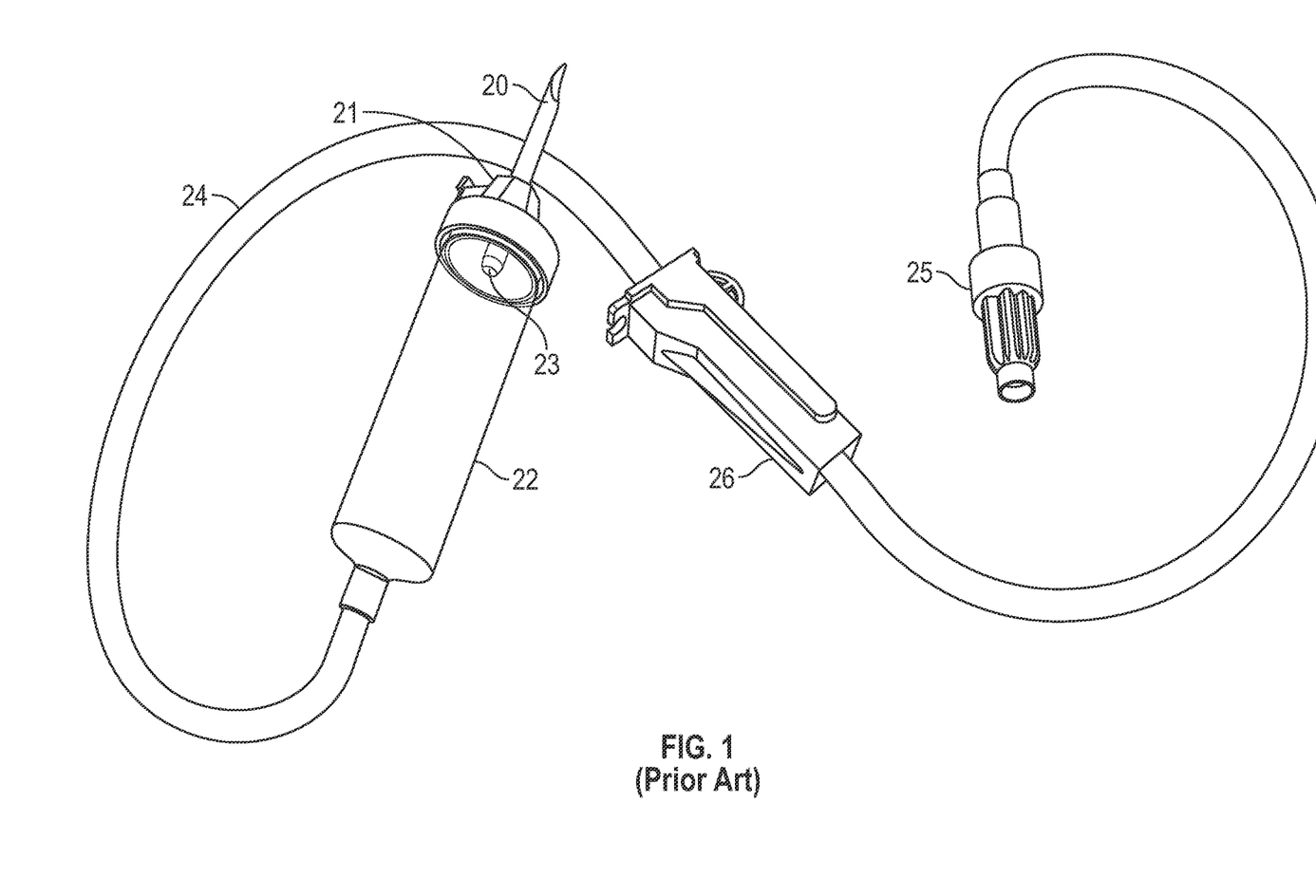
FIG. 1 depicts a perspective view of an example infusion set having a typical roller clamp.

The present disclosure relates to a roller clamp and in particular to a roller clamp for use in gravity infusion. The roller clamp regulates the flow rate of a medical fluid (for example a solution of a drug to be administered to a patient, or blood) flowing through a tube. Typically, a standard infusion set is used to infuse the fluid. An example of a standard infusion set is shown in FIG. 1.

The infusion set includes a piercing spike 20 which may either be a sharp spike for piercing rubber stoppers or rounded and blunt for insertion into a bag. The spike contains one channel for fluid and optionally a second channel for venting. A vent 21 is usually present in the vicinity of the piercing spike to allow air to flow into the drop chamber 22. The vent 21 may be provided with a bacterial filter to prevent bacteria from entering the equipment.

The drop chamber 22 has a drop generator 23 at the top of the drop chamber 22 that produces drops of a certain size. Drops from the drop generator 23 fall into the drop chamber 22 such that the drop chamber 22 is partially filled with liquid. This prevents air bubbles from entering the connector tube 24, which would be harmful to a patient. A particle filter may be provided at the lower aperture of the drop chamber 22.

The connector tube 24 connects the drop chamber 22 with the patient. The connector tube 24 is usually around 150 cm long and can be manufactured from PVC. The tube 24 is shown shortened in FIG. 1 for clarity. The connector tube 24 typically has a continuous diameter throughout the length of the tube.

At the end of the connector tube 24 is a Luer fitting 25 which is standardized for connection to all other pieces of apparatus having a standard Luer cone. The person skilled in the art will appreciate that the Luer fitting 25 can be fitted to a hypodermic needle (not shown) for infusing the medical fluid into the circulatory system of a patient (e.g., into a vein).

Between the drop chamber 22 and the Luer fitting 25 and engaging with the connector tube 24, is a roller clamp 26. The present disclosure is concerned with an improved roller clamp assembly, but a typical roller clamp 26 as known in the art will now be described for background information.

Figure 2:
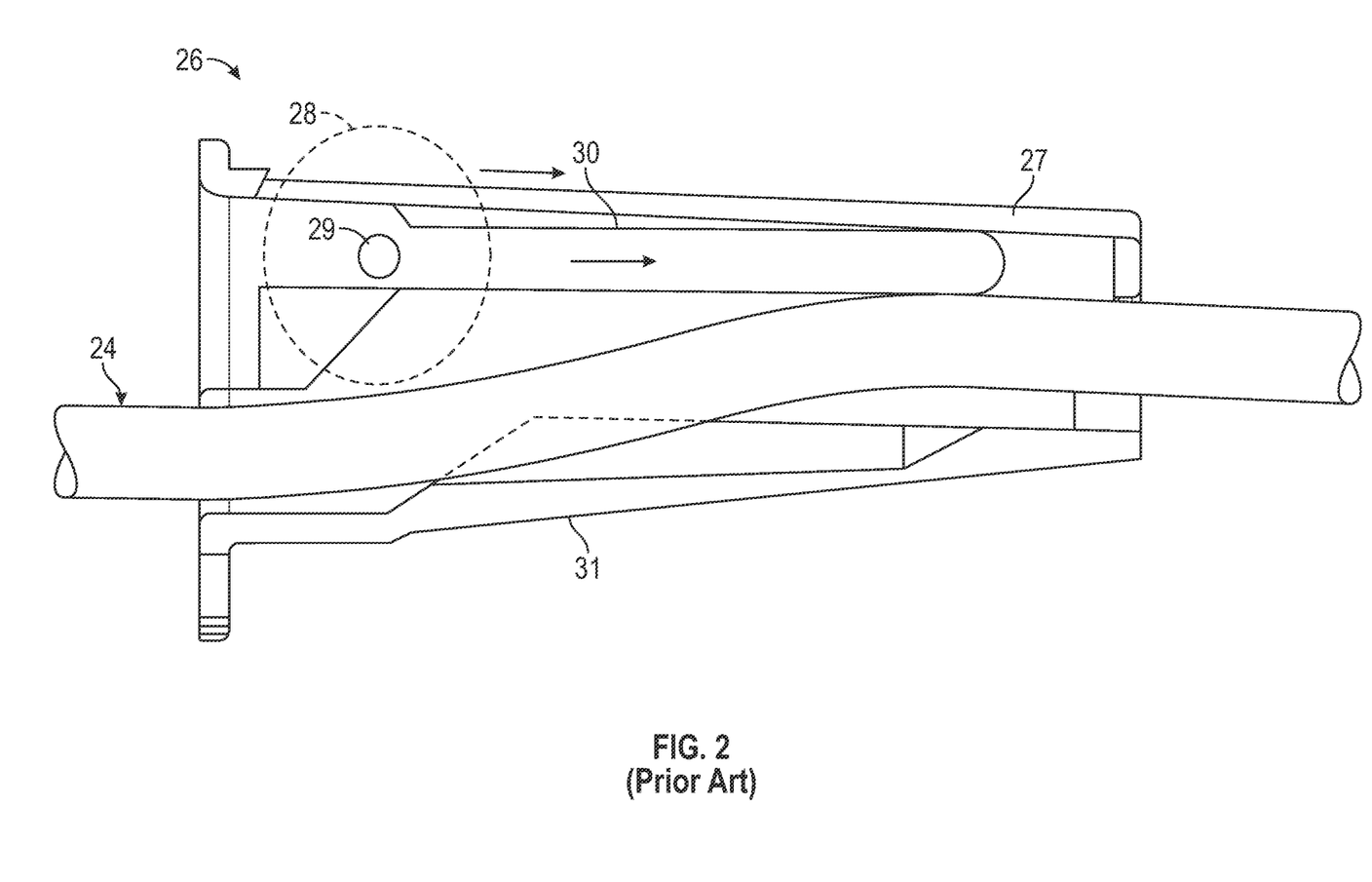
FIG. 2 depicts a cross-section side view of the roller clamp of FIG. 1.

The roller clamp 26 illustrated in FIG. 2 has two opposing side walls 27 having a pair of guide grooves 30 that are aligned with each other and face each other. A flow-regulating roller 28 is provided having axially-projecting shafts 29 protruding from the centers of each side of the roller 28. The roller 28 is shown in outline for clarity. The shafts 29 of the roller 28 are captured by and seated in the guide grooves 30 so that the roller 28 can move up and down the guide grooves 30 as indicated by the arrows in FIG. 2.

The entire roller clamp 26 has four walls (see FIG. 1) in an open-ended boxlike construction and is dimensioned and configured to receive the connector tube 24. In use, the tube 24 passes through the roller clamp 26, between the two opposing side walls 27, the roller 28 and a guide wall 31 that is opposed to the roller 28.

In the roller clamp 26, the surface of the guide wall 31 converges along its length toward the position of the guide grooves 30 in the downward direction of the guide grooves 30 (e.g., in the direction of the arrows in FIG. 2). This tends to urge the connector tube 24 within the roller clamp 26 toward the guide grooves 30 and thus toward roller 28.

Thus, rolling the roller 28 downwardly along the guide grooves 30 in the direction of the gradually closer guide wall 31 in the direction of the arrows causes the roller 28 to impinge against the connector tube 24. As the roller 28 impinges on the tube 24, the tube 24 becomes squeezed, as it is a flexible material such as PVC, and the lumen of the infusion tube 24 therefore becomes smaller. In this way, by narrowing of the lumen, the flow rate of liquid passing through the connector tube 24 can be regulated.

Thus, the roller clamp 26 controls the flow rate through the infusion tube 24 by clamping the infusion tube 24 between the roller 28 and the guide wall 31. As discussed above, this provides for a course flow rate change because a small movement of the roller 28 causes a large change in the flow rate of the fluid through the tube 24. Also, the force of the fluid in the tube 24 exerts a biasing force against the roller 28, which often leads to slippage of the roller 28 (e.g., the roller 28 rolls back) from the adjusted position. In addition, the roller clamp 26 requires manual adjustment and is not suitable for automated or processor controlled adjustment.

With reference to FIGS. 3-9, a circular roller clamp assembly 100 is shown mounted to an IV pole 190. The circular roller clamp assembly 100 has a housing 110 having a semi-circular construction and is dimensioned and configured to receive tubing, such as connector tube 24 (see FIG. 4). Two opposing side walls 112 define a guide groove 120 that receives a flow-regulating roller 130 that is disposed on an axially-projecting shaft 132 coupled to a motor arm 140 of a motor 150. The shaft 132 is positioned outside outer peripheral walls 114 of the housing 110 so that the roller 130 can move circumferentially along and within the guide groove 120.

Figure 6:
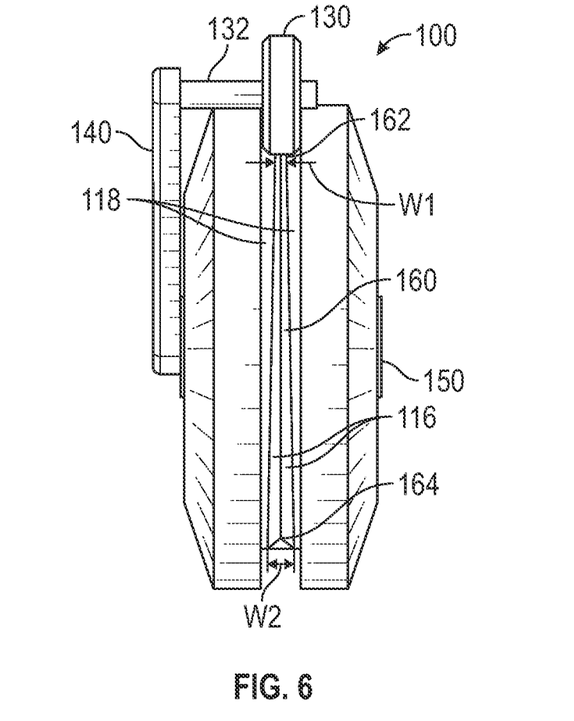
FIG. 6 depicts a front view of the circular roller clamp assembly of FIG. 3, according to aspects of the disclosure.

Two inner peripheral walls 116 extend inward from the opposing side walls 112 and are disposed circumferentially within the guide groove 120. For example, outer peripheral surfaces 118 of the inner peripheral walls 116 may form a base surface 122 (e.g., bottom surface) of the guide groove 120. The inner peripheral walls 116 define a tube channel 160 having a varying width and/or depth along the circumferential path of the tube channel 160. For example, a top end 162 of the tube channel 160 may have a narrow width W1 and a bottom end 164 of the tube channel 160 may have a wide width W2. The inner peripheral walls 116 may be planar and angle inward from the base surface 122 until they intersect one another, thus causing the tube channel 160 to have a triangular shape (as shown in FIG. 6). In aspects of the disclosure, the inner peripheral walls 116 may be curved (e.g., convex, concave) or any other suitable geometry. For example, the inner peripheral walls 116 may be concavely curved such that the tube channel 160 forms a U shape.

Figure 7:
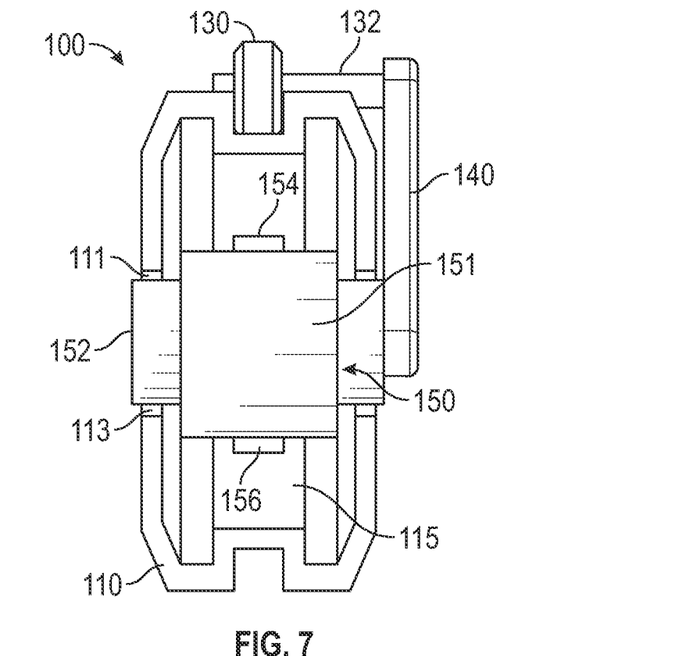
FIG. 7 depicts a rear view of the circular roller clamp assembly of FIG. 3, according to aspects of the disclosure.
Figure 8:
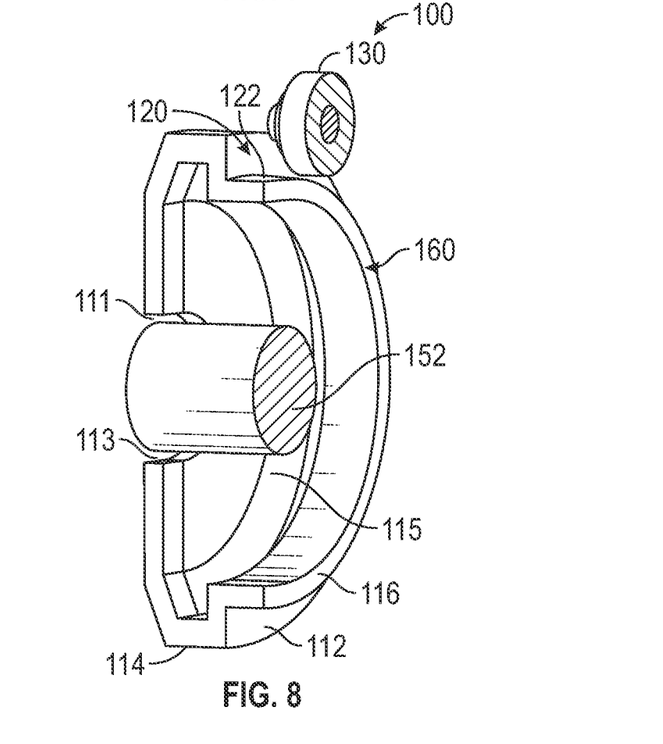
FIG. 8 depicts a cross-section perspective view of the circular roller clamp assembly of FIG. 3, according to aspects of the disclosure.

The motor 150 may be provided as a central axis of the housing 110. For example, as shown in FIG. 7, the motor 150 may have a motor housing 151 disposed within a cavity 115 of the housing 110 and a cylindrical shaft 152 that is disposed within a central bore 111 of the housing 110 such that there is a peripheral gap 113 between the cylindrical shaft 152 and the central bore 111. The peripheral gap 113 allows for unimpeded rotation of the cylindrical shaft 152 within the central bore 111. Rotation of the cylindrical shaft 152 causes the motor arm 140 to rotate, which thus causes the shaft 132 and the roller 130 to move along the circumference of the housing 110. A power interface 154 and a data interface 156 may be positioned on the motor 150 to receive power from a power source and to receive/send communications signals to and/or from processors and sensors. The power interface 154 and/or the data interface 156 may be wired or wireless. In aspects of the disclosure, the motor 150 may have its own power source (e.g., a battery) and/or a wireless communications interface.

Figure 9:
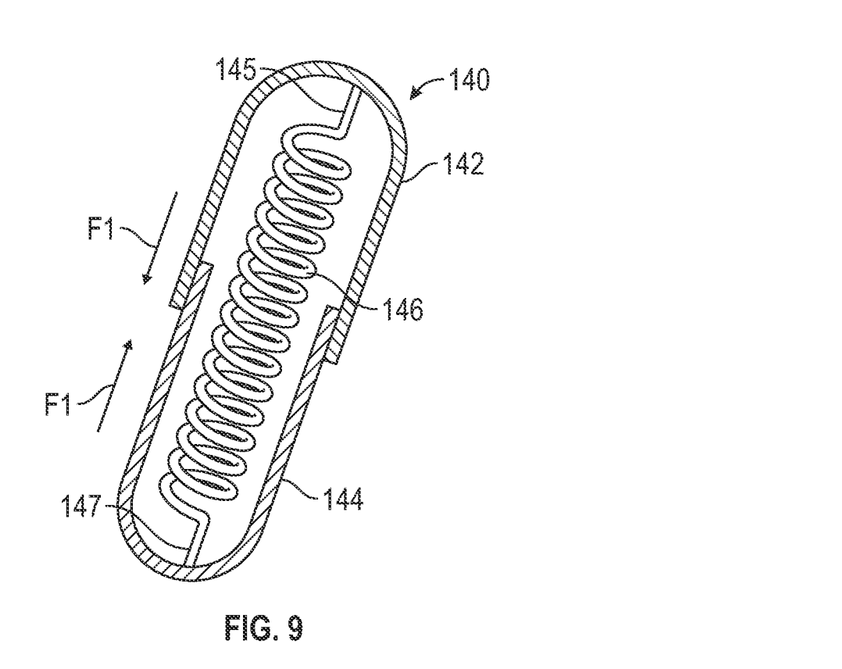
FIG. 9 depicts a cross-section perspective view of a motor arm of a circular roller clamp assembly, according to aspects of the disclosure.

As shown in FIG. 9, the motor arm 140 may include two arm sections 142, 144 and a spring 146, where a first spring end 145 is coupled to the first arm section 142 and a second spring end 147 is coupled to the second arm section 144. The arm sections 142, 144 may be slidably moveable relative to each other such that when the arm sections 142, 144 are moved in directions away from each other, the spring 146 stretches. The stretched spring 146 provides a biasing force F1 on the arm sections 142, 144 to move the arm sections 142, 144 back towards an engaged position.

In use, the motor arm 140 may be pulled in an outward direction away from the cylindrical shaft 152 so that the roller 130 is completely outside of the guide groove 120. Tube 24 may then be fed into the guide groove 120 such that the tube 24 follows the cylindrical path of the guide groove 120 from the top end 162 of the tube channel 160 to the bottom end 164 of the tube channel 160. The motor arm 140 may then be released so that the motor arm 140 contracts (e.g., arm sections 142, 144 move closer towards each other due to biasing force F1) and the roller 130 engages the tube 24. Thus, the tube 24 passes through the roller clamp assembly 100, between the two opposing side walls 112, the roller 130 and the tube channel 160 that is opposed to the roller 130.

Moving the roller 130 circumferentially along the guide groove 120 in the direction of the top end 162 of the tube channel 160 causes the roller 130 to impinge more forcefully against the tube 24 as less of the tube 24 fits within the narrower portion of the tube channel 160. As the roller 130 impinges more forcefully on the tube 24, the tube 24 is further squeezed, as it is a flexible material such as PVC, and the lumen (e.g., fluid flow path) of the infusion tube 24 therefore becomes smaller, thus reducing the fluid flow rate through the tube 24.

Similarly, moving the roller 130 circumferentially along the guide groove 120 in the direction of the bottom end 164 of the tube channel 160 causes the roller 130 to impinge less forcefully against the tube 24 as more of the tube 24 fits within the wider portion of the tube channel 160. As the roller 130 impinges less forcefully on the tube 24, the tube 24 is less squeezed and the lumen of the infusion tube 24 becomes larger, thus increasing the fluid flow rate through the tube 24. In this way, by narrowing and expanding the lumen of the tube 24, the flow rate of liquid passing through the tube 24 can be regulated.

Figure 3:
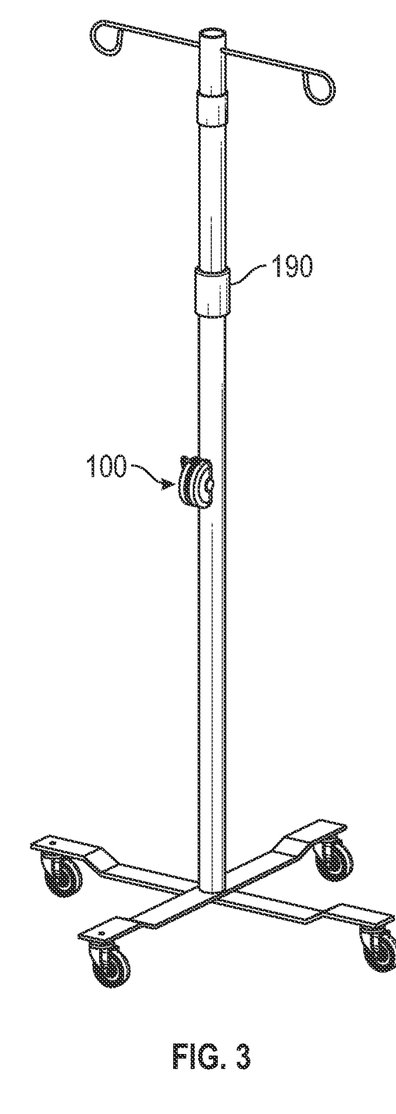
FIG. 3 depicts a perspective view of an IV pole with a circular roller clamp assembly, according to aspects of the disclosure.
Figure 4:
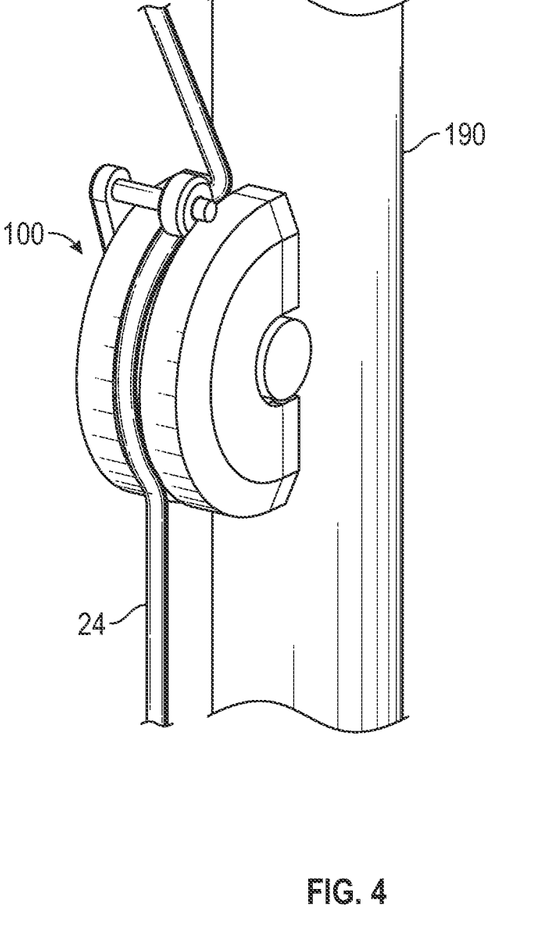
FIG. 4 depicts a perspective view of the IV pole with a circular roller clamp assembly of FIG. 3, according to aspects of the disclosure.
Figure 5:
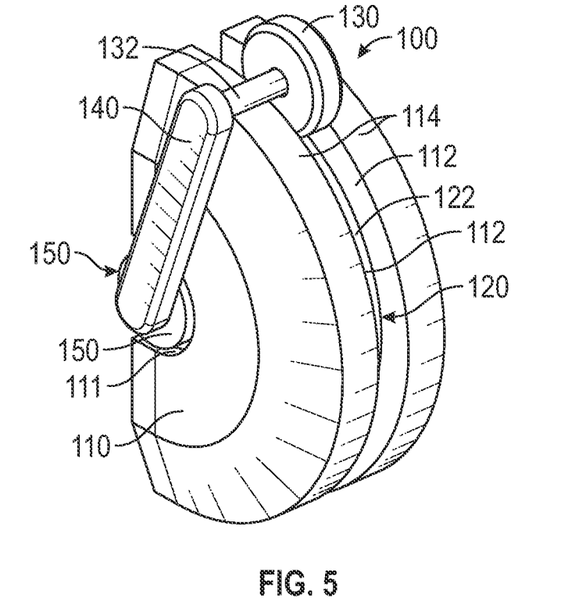
FIG. 5 depicts a perspective view of the circular roller clamp assembly of FIG. 3, according to aspects of the disclosure.

As an example, as shown in FIG. 3, the circular roller clamp assembly 100 may be mounted to IV pole 190 with the power interface 154 and data interface 156 connected to power wires and communications cables (not shown) disposed inside the IV pole 190. A user (e.g., health care clinician) may pull the spring loaded motor arm 140 outward from the housing 110 and position IV tube 24 into the guide groove 120 along the tube channel 160. The user may then release the motor arm 140 so that the biasing force F1 of the spring 146 pulls the roller 130 inward against the IV tube 24, pressing the IV tube 24 against the tube channel 160. The motor 150 may communicate with an external flow sensor and rotate the motor arm 140 to position the roller 130 along the tube channel 160 to achieve the necessary compression of the IV tube 24 for the desired fluid flow rate through the IV tube 24. In aspects of the disclosure, the motor 150 may be configured to be manually adjustable so that a user may manually select the position of the roller 130 for high resolution flow setpoint selection.

The circular geometry of the circular roller clamp assembly 100 significantly increases the length of the flow control channel (e.g., semi-circular tube channel 160 versus the linear channel through roller clamp 26), thus enabling a much larger flow control resolution. For example, the semi-circular tube channel 160 may have a 300% increase in length over the linear length of the roller clamp 26. The circular geometry also allows for a simple motor 150 to be used to control the operation of the circular roller clamp assembly 100.

According to aspects of the disclosure, the circular roller clamp assembly 100 may be configured to hang on a bracket attached to the IV pole 190. According to aspects of the disclosure, the circular roller clamp assembly 100 may be configured to hang directly on an IV line (e.g., tube 24). According to aspects of the disclosure, the circular roller clamp assembly 100 may include a coupling mechanism on or adjacent a mounting surface 119 of the housing 110. For example, the housing 110 may include one or more magnets within or on the mounting surface 119 or portions of the mounting surface 119 may be formed of a magnetic material, such that the circular roller clamp assembly 100 may be quickly and easily attached to any magnetic surface (e.g., metal pole, metal bed handrail, metal shelf). As another example, the coupling mechanism may be a clamping device configured to clamp to a desired surface (e.g., IV pole, bedrail, shelf, table).

According to aspects of the disclosure, the circular roller clamp assembly 100 may be configured to integrate with a smart controller. For example, the circular roller clamp assembly 100 may be integrated into a controller housing, where the controller may receive input from one or more sensors (e.g., downstream flow rate sensor) and send control signals to the motor 150 based on the sensor input and/or programmed parameters (e.g., flow settings input by a user or another processor). As another example, the circular roller clamp assembly 100 may include its own smart controller that can directly receive sensor information, determine a position of the roller 130 that will achieve the desired flow rate and/or send control signals to the motor 150 to position the roller 130 in the determined position. According to aspects of the disclosure, the circular roller clamp assembly 100 may communicate with internal or external sensors/controllers/processors via wired and/or wireless communications.

Figure 10:
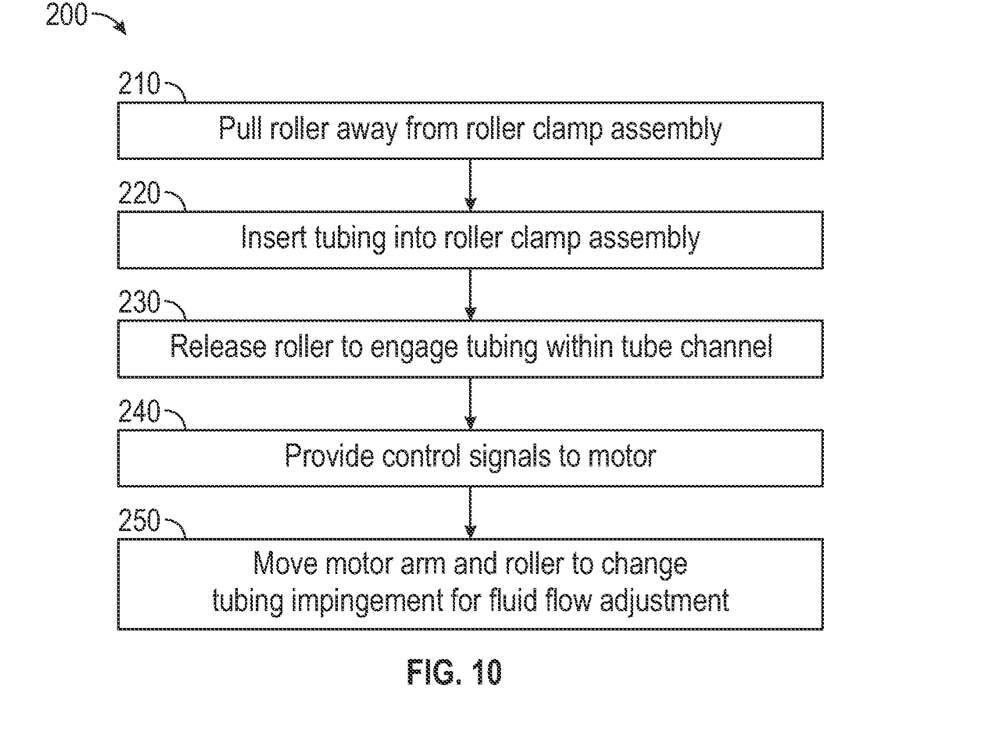
FIG. 10 illustrates a method of operating a circular roller clamp assembly, according to aspects of the disclosure.

With reference to FIG. 10, a method 200 of operating a circular roller clamp assembly (e.g., circular roller clamp assembly 100) is provided. In step 210, the roller (e.g., roller 130) is pulled away from the housing (e.g., housing 110). For example, a motor arm (e.g., motor arm 140) may be expandable via spring loaded slidable portions (e.g., arm sections 142, 144 and spring 146), thus allowing the roller coupled to the motor arm to be pulled with a force that exceeds the biasing force (e.g., biasing force F1) of the spring. Tubing (e.g., IV tube 24) is placed or inserted into the housing such that the tubing is disposed within a housing channel (e.g., tube channel 160 within guide groove 120), in step 220.

In step 230, the roller is released to pull back and engage the tubing. For example, the release of the roller allows the biasing force of the spring to contract the motor arm, thus pulling the roller into the housing channel so that the roller engages and compresses the tubing into the housing channel. Control signals may be provided to the motor (e.g., motor 150) to direct the motor to move the roller to a specific position on the housing, in step 240. For example, the motor may monitor sensor signals and adjust the roller position in order to change the fluid flow rate to a desired flow rate. Here, positioning the roller near a first end of the channel housing (e.g., top end 162 of the tube channel 160) may cause the roller to impinge the tubing to a great degree (e.g., zero or minimal fluid flow), while positioning the roller near a second end of the channel housing (e.g., bottom end 164 of the tube channel 160) may cause the roller to impinge the tubing to a very low degree (e.g., full or maximum fluid flow).

In step 250, the roller may be moved along the housing channel by the motor to impinge the tubing at the desired level. For example, the roller may be moved from the second end of the channel housing to the first end of the channel housing so that a narrowing between the housing channel and the roller causes the roller to compress or squeeze the contacted portion of the tubing, thus causing the fluid flow rate in the tubing to change to a lower or blocked flow rate (e.g., from 250 ml/hr to 0 ml/hr). Similarly, moving the roller along the housing channel in the opposing direction will cause the fluid flow rate to change to a higher or open flow rate (e.g., from 0 ml/hr to 250 ml/hr). Thus, positioning the roller in various positions between the first and second ends of the channel housing will vary the fluid flow rate accordingly (e.g., 50 ml/hr, 100 ml/hr, 150 ml/hr, 200 ml/hr).

In one or more embodiments, a circular roller clamp assembly comprises: a semi-circular housing configured to receive a portion of an IV tube; a motor; a motor arm coupled to the motor; and a roller coupled to the roller arm, the roller configured to be movably received by a guide groove disposed in the semi-circular housing, wherein the circular roller clamp assembly is configured to regulate a flow rate of fluid flowing through the IV tube based on engagement of the roller with the IV tube via circumferential movement of the roller along the guide groove.

In aspects of the disclosure, the guide groove comprises two opposing side walls extending radially inward from a perimeter surface of the semi-circular housing and a base surface disposed at an inward end of the side walls. In aspects of the disclosure, the semi-circular housing comprises two inner peripheral walls extending radially inward from the base surface of the guide groove and defining a tube channel configured to receive a portion of the IV tube. In aspects of the disclosure, the tube channel comprises a varying width from a first width at a first end to a second width at a second end, the second width being wider than the first width. In aspects of the disclosure, the tube channel comprises a varying depth from a first depth at a first end to a second depth at a second end, the second depth being deeper than the first depth. In aspects of the disclosure, the inner peripheral walls extend radially inward from the base surface of the guide groove at an acute angle and intersect with one another to define the tube channel as a triangular shape.

In aspects of the disclosure, a cylindrical shaft of the motor is disposed within a central bore of the semi-circular housing and a peripheral gap is disposed between the cylindrical shaft and the central bore, wherein the motor arm is coupled to an end of the cylindrical shaft, and wherein the cylindrical shaft is configured to rotate unimpeded within the central bore. In aspects of the disclosure, a power interface is disposed on the motor, the power interface configured to receive power from a power source. In aspects of the disclosure, a communications interface is disposed on the motor, the communications interface configured to one of send communications signals to one of a processor and a sensor and receive communications signals from one of a processor and a sensor.

In aspects of the disclosure, the motor arm comprises: a first arm section; a second arm section movably coupled to the first arm section; and a spring having a first spring end coupled to the first arm section and a second spring end coupled to the second arm section, wherein the spring is configured to stretch to provide for opposing movement of the first arm section relative to the second arm section and to provide a biasing contracting force to pull the first arm section and the second arm section towards one another towards a base position. In aspects of the disclosure, the motor arm is configured to extend so that the roller is positioned outside of the guide groove for insertion of the IV tube into the guide groove, and wherein the motor arm is configured to contract due to the biasing force of the spring to pull the roller against the IV tube. In aspects of the disclosure, the semi-circular housing is configured to be mounted on an IV pole. In aspects of the disclosure, the circular roller clamp assembly comprises a magnetic coupler configured to mount to a magnetic surface. In aspects of the disclosure, the circular roller clamp assembly is configured to hang from the IV tube.

In one or more embodiments, an IV set comprises: an IV tube configured to be coupled to a fluid container; an infusion component coupled to the IV tube; and a circular roller clamp assembly coupled to the IV tube, the circular roller clamp assembly comprising: a semi-circular housing configured to receive the IV tube; a motor; a motor arm coupled to the motor; and a roller coupled to the roller arm, the roller configured to be movably received by a guide groove disposed in the semi-circular housing, wherein the circular roller clamp assembly is configured to regulate a flow rate of fluid flowing through the IV tube based on engagement of the roller with the IV tube via circumferential movement of the roller along the guide groove.

In aspects of the disclosure, the guide groove comprises two opposing side walls extending radially inward from a perimeter surface of the semi-circular housing and a base surface disposed at an inward end of the side walls, the semi-circular housing comprises two inner peripheral walls extending radially inward from the base surface of the guide groove and defining a tube channel configured to receive a portion of the IV tube, and the tube channel comprises one of: a varying width from a first width at a first end to a second width at a second end, the second width being wider than the first width; and a varying depth from a first depth at the first end to a second depth at the second end, the second depth being deeper than the first depth.

In aspects of the disclosure, the motor arm comprises: a first arm section; a second arm section movably coupled to the first arm section; and a spring coupled to the first arm section and to the second arm section, the spring configured to stretch to provide for opposing movement of the first arm section relative to the second arm section and to provide a biasing contracting force to pull the first arm section and the second arm section towards one another, wherein the motor arm is configured to extend so that the roller is positioned outside of the guide groove for insertion of the IV tube into the guide groove, and wherein the motor arm is configured to contract due to the biasing force of the spring to pull the roller against the IV tube.

In one or more embodiments, a method of operating a circular roller clamp assembly comprises: pulling a roller coupled to an extendable motor arm radially outward from a guide groove disposed in a perimeter surface of a semi-circular housing of the circular roller clamp assembly; placing an intravenous (IV) tube between roller and the guide groove; releasing the roller wherein a biasing force of a spring of the motor arm contracts the motor arm radially inward towards the IV tube and the guide groove; pressing, by the roller, the IV tube against a varying sized tube channel disposed within the guide groove; rotating, by a motor, the motor arm in a first direction to move the roller towards a smaller sized portion of the tube channel to increase impingement of the IV tube by the roller and decrease a rate of fluid flow through the IV tube; and rotating, by the motor, the motor arm in a second direction to move the roller towards a larger sized portion of the tube channel to decrease impingement of the IV tube by the roller and increase the rate of fluid flow through the IV tube.

In aspects of the disclosure, the method comprises monitoring, by a sensor, the rate of fluid flow through the IV tube; and providing control signals from a processor to the motor to rotate the motor arm to adjust a position of the roller to change the rate of fluid flow to a determined rate. In aspects of the disclosure, the method comprises wherein positioning the roller at a smallest sized portion of the tube channel causes the roller to occlude the IV tube and prevent any fluid flow through the IV tube downstream of the occlusion; and wherein positioning the roller at a largest sized portion of the tube channel causes the roller to not impinge the IV tube and provide full fluid flow through the IV tube downstream of the roller.

It is understood that any specific order or hierarchy of blocks in the methods of processes disclosed is an illustration of example approaches. Based upon design or implementation preferences, it is understood that the specific order or hierarchy of blocks in the processes may be rearranged, or that all illustrated blocks be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A circular roller clamp assembly comprising:
    a semi-circular housing configured to receive a portion of an intravenous (IV) tube;
    a motor;
    a motor arm coupled to the motor; and
    a roller coupled to the motor arm, the roller configured to be movably received by a guide groove disposed in the semi-circular housing,
    wherein the circular roller clamp assembly is configured to regulate a flow rate of fluid flowing through the IV tube based on engagement of the roller with the IV tube via circumferential movement of the roller along the guide groove.

2. The circular roller clamp assembly of claim 1, wherein the guide groove comprises:
    two opposing side walls extending radially inward from a perimeter surface of the semi-circular housing; and
    a base surface disposed at an inward end of the side walls.

3. The circular roller clamp assembly of claim 2, wherein the semi-circular housing comprises:
    two inner peripheral walls extending radially inward from the base surface of the guide groove and defining a tube channel configured to receive a portion of the IV tube.

4. The circular roller clamp assembly of claim 3, wherein the tube channel comprises a varying width from a first width at a first end to a second width at a second end, the second width being wider than the first width.

5. The circular roller clamp assembly of claim 3, wherein the tube channel comprises a varying depth from a first depth at a first end to a second depth at a second end, the second depth being deeper than the first depth.

6. The circular roller clamp assembly of claim 3, wherein the inner peripheral walls extend radially inward from the base surface of the guide groove at an acute angle and intersect with one another to define the tube channel as a triangular shape.

7. The circular roller clamp assembly of claim 1, further comprising:
    a cylindrical shaft of the motor disposed within a central bore of the semi-circular housing; and
    a peripheral gap disposed between the cylindrical shaft and the central bore,
    wherein the motor arm is coupled to an end of the cylindrical shaft, and
    wherein the cylindrical shaft is configured to rotate unimpeded within the central bore.

8. The circular roller clamp assembly of claim 1, further comprising:
    a power interface disposed on the motor, the power interface configured to receive power from a power source.

9. The circular roller clamp assembly of claim 1, further comprising:
    a communications interface disposed on the motor, the communications interface configured to one of:
        send communications signals to one of a processor and a sensor; and
        receive communications signals from one of the processor and the sensor.

10. The circular roller clamp assembly of claim 1, wherein the motor arm comprises:
    a first arm section;
    a second arm section movably coupled to the first arm section; and
    a spring having a first spring end coupled to the first arm section and a second spring end coupled to the second arm section,
    wherein the spring is configured to stretch to provide for opposing movement of the first arm section relative to the second arm section and to provide a biasing contracting force to pull the first arm section and the second arm section towards one another towards a base position.

11. The circular roller clamp assembly of claim 10, wherein the motor arm is configured to extend so that the roller is positioned outside of the guide groove for insertion of the IV tube into the guide groove, and wherein the motor arm is configured to contract due to the biasing force of the spring to pull the roller against the IV tube.

12. The circular roller clamp assembly of claim 1, wherein the semi-circular housing is configured to be mounted on an IV pole.

13. The circular roller clamp assembly of claim 1, wherein the circular roller clamp assembly comprises a magnetic coupler configured to mount to a magnetic surface.

14. The circular roller clamp assembly of claim 1, wherein the circular roller clamp assembly is configured to hang from the IV tube.

15. An intravenous (IV) set comprising:
    an IV tube configured to be coupled to a fluid container;
    an infusion component coupled to the IV tube; and
    a circular roller clamp assembly coupled to the IV tube, the circular roller clamp assembly comprising:
        a semi-circular housing configured to receive the IV tube;
        a motor;
        a motor arm coupled to the motor; and
        a roller coupled to the motor arm, the roller configured to be movably received by a guide groove disposed in the semi-circular housing,
    wherein the circular roller clamp assembly is configured to regulate a flow rate of fluid flowing through the IV tube based on engagement of the roller with the IV tube via circumferential movement of the roller along the guide groove.

16. The IV set of claim 15, wherein the guide groove comprises two opposing side walls extending radially inward from a perimeter surface of the semi-circular housing and a base surface disposed at an inward end of the side walls, wherein the semi-circular housing comprises two inner peripheral walls extending radially inward from the base surface of the guide groove and defining a tube channel configured to receive a portion of the IV tube, and wherein the tube channel comprises one of:

a varying width from a first width at a first end to a second width at a second end, the second width being wider than the first width; and a varying depth from a first depth at the first end to a second depth at the second end, the second depth being deeper than the first depth.

17. The IV set of claim 15, wherein the motor arm comprises:

a first arm section;

a second arm section movably coupled to the first arm section; and a spring coupled to the first arm section and to the second arm section, the spring configured to stretch to provide for opposing movement of the first arm section relative to the second arm section and to provide a biasing contracting force to pull the first arm section and the second arm section towards one another, wherein the motor arm is configured to extend so that the roller is positioned outside of the guide groove for insertion of the IV tube into the guide groove, and wherein the motor arm is configured to contract due to the biasing force of the spring to pull the roller against the IV tube.

18. A method of operating a circular roller clamp assembly, the method comprising:

pulling a roller coupled to an extendable motor arm radially outward from a guide groove disposed in a perimeter surface of a semi-circular housing of the circular roller clamp assembly;

placing an intravenous (IV) tube between roller and the guide groove;

releasing the roller wherein a biasing force of a spring of the motor arm contracts the motor arm radially inward towards the IV tube and the guide groove;

pressing, by the roller, the IV tube against a varying sized tube channel disposed within the guide groove;

rotating, by a motor, the motor arm in a first direction to move the roller towards a smaller sized portion of the tube channel to increase impingement of the IV tube by the roller and decrease a rate of fluid flow through the IV tube; and rotating, by the motor, the motor arm in a second direction to move the roller towards a larger sized portion of the tube channel to decrease impingement of the IV tube by the roller and increase the rate of fluid flow through the IV tube.

19. The method of claim 18, further comprising:

monitoring, by a sensor, the rate of fluid flow through the IV tube; and providing control signals from a processor to the motor to rotate the motor arm to adjust a position of the roller to change the rate of fluid flow to a determined rate.

20. The method of claim 18, further comprising:

wherein positioning the roller at a smallest sized portion of the tube channel causes the roller to occlude the IV tube and prevent any fluid flow through the IV tube downstream of the occlusion; and wherein positioning the roller at a largest sized portion of the tube channel causes the roller to not impinge the IV tube and provide full fluid flow through the IV tube downstream of the roller.

\* \* \* \* \*